United States Patent [19]

Simon et al.

[11] Patent Number: 4,738,840

[45] Date of Patent: * Apr. 19, 1988

[54] PRESURGICAL STERILIZATION METHOD

[76] Inventors: Gilbert I. Simon, 1111 Midland Ave., Bronxville, N.Y. 10708; Roy T. Witkin, 23 Broadview Rd., Westport, Conn. 06880

[*] Notice: The portion of the term of this patent subsequent to Jun. 4, 2002 has been disclaimed.

[21] Appl. No.: 902,430

[22] Filed: Aug. 29, 1986

Related U.S. Application Data

[60] Continuation-in-part of Ser. No. 835,378, Mar. 3, 1986, which is a division of Ser. No. 763,469, Aug. 7, 1985.

[51] Int. Cl.$^4$ .................. A01N 59/12; A61K 7/20; A61K 33/18; A61K 33/40
[52] U.S. Cl. ............................ 424/51; 424/130; 424/150; 422/29; 422/37; 433/215
[58] Field of Search .................. 433/215, 226; 422/12, 422/28, 29, 37; 424/130, 150, 51, 53

[56] References Cited

U.S. PATENT DOCUMENTS

| | | | |
|---|---|---|---|
| 3,018,778 | 1/1962 | Brilliant | 433/226 X |
| 4,054,998 | 10/1977 | Hesselgren | 422/28 X |
| 4,329,333 | 5/1982 | Barr | 424/54 X |
| 4,521,403 | 6/1985 | Simon et al. | 424/150 X |
| 4,567,036 | 1/1986 | Simon et al. | 424/150 X |
| 4,592,487 | 6/1986 | Simon et al. | 222/94 |
| 4,592,488 | 6/1986 | Simon et al. | 222/94 |
| 4,592,489 | 6/1986 | Simon et al. | 222/94 |

FOREIGN PATENT DOCUMENTS

| | | | |
|---|---|---|---|
| 2320990 | 10/1974 | Fed. Rep. of Germany | 422/24 |
| 2438594 | 2/1976 | Fed. Rep. of Germany | 424/150 |
| 2718385 | 11/1978 | Fed. Rep. of Germany | 424/150 |

OTHER PUBLICATIONS

Kirk-Othmer, Encyclopedia of Chemical Technology, 7, pp. 802–803, 13, pp. 649–655 and 660–674.
The Merck Index, 10th Ed., Merck & Co., Inc. (1983), Rahway, N.J., p. 697.

*Primary Examiner*—David L. Lacey
*Assistant Examiner*—Jill Johnston
*Attorney, Agent, or Firm*—Jacobs & Jacobs

[57] ABSTRACT

Pre- and post-operative dental and surgical procedures in and on structures and areas of the oral cavity are maintained sterile by the application thereto of an antimicrobially enhanced aqueous solution of an iodophor constituting a source of iodine and a peroxide as a source of oxygen, the aqueous solution ensuring sterility of the structures and areas in the oral cavity before, during and after the operating procedures therein and retarding or inhibiting microbial regrowth on and in the structures and areas in a dental or surgical environment. The iodophor is preferably a povidone iodine complex soluble in water and the peroxide is preferably hydrogen peroxide, the oxygen from the peroxide acting to enhance the antimicrobial activity of the iodine derived from the povidone iodine complex.

7 Claims, No Drawings

PRESURGICAL STERILIZATION METHOD

This application is a continuation-in-part of our application Serial No. 835,378 filed Mar. 3, 1986 which is a division of our application Serial No. 763,469 filed Aug. 7, 1985.

In our said applications, the contents of which are hereby made a part hereof by reference, we have described the sterilization of dental and surgical instruments and appliances and the presurgical sterilization of actual or potential sites on and in the human or animal body. In those applications we have found it essential to ensure sterile conditions prior to, during and after the dental and surgical or other operative procedures and also those relating to human skin sites and to inhibit the presence or growth of microorganisms in the human oral cavity during use of the sterilized dental and surgical instruments and appliances whether such be carried out in a dental or surgical environment.

The preparation and use of an oral lavage having antimicrobially enhanced activity in the oral cavity is known from our U.S. Pat. Nos. 4,521,403, 4,567,036, 4,592,487, 4,592,488 and 4,592,489 and in accordance with those patents the antimicrobial activity of the iodine derived in aqueous solution of a source of iodine is enhanced by the nascent or active oxygen available from the source of oxygen and such enhancement has therein been well established.

It has now been found that treatment of oral cavity pre- or post-operative structures and areas with an aqueous solution of an iodophor containing a source of elemental iodine and a source of nascent or active oxygen, for example, an iodophor such as povidone iodine and a peroxide such as $H_2O_2$, ensures sterility of the structure and area, or the prepared site or location where the surgical operation is to be or has been carried out and this makes it possible to carry out the dental or surgical operation in the absence of living microorganisms. The aqueous solution is preferably used and is most effective when newly prepared from the source of iodine and the source of oxygen and which are maintained out of contact with one another until such time as they are to be combined and applied to the area or location at which the operating procedure is to be or has been carried out.

The primary objective of the present invention is to extend the uses of the antimicrobially enhanced solution in new and unobvious ways dealing mainly but not exclusively with dental surgery and the carrying out of known surgical/dental procedures and operations under sterile conditions which protect both the patient being operated upon and the dental surgeon, in the event the patient may have some infection or disease which could be contagious or transmitted to the dental surgeon who, under such circumstances, would wear a sterile, suitable surgical or gauze facial mask, drape, gloves or garment.

The present invention is further concerned with the carrying out of the dental or surgical operations under conditions where bacteria or microorganisms normally form plaque or other undesired deposits on or in human teeth such as scale, decayed matter and root canal excavation preparatory to filling or packing the resulting cleaned tooth cavities and canals with a temporary or permanent protective gummy or other plastic filling which hardens. The invention is furthermore broadly applicable to prosthetic and orthodontic dental devices, to tooth implants, to the high speed, small amplitude vibratory devices for use in scaling teeth and in general to various dental and surgical operations taking place in the mouth.

The invention particularly concerns the chemical sterilization of natural and artificial structures and areas in the oral cavity of a dental or surgical patient by applying the povidone iodine-peroxide aqueous solution to all or selected surfaces of said structures or areas at one or more pre-selected times. By the term "natural and artificial structures and areas" as used herein is meant, but without limitation thereto, partial or entire dentures, braces, tooth implants and cavities, prosthetic and orthodontic devices, decayed teeth areas, loosened teeth and malocclusions, the removal of accumulated scale from dental surfaces, high speed low amplitude drilling of decayed teeth areas, either in the body of the teeth or in their root canals. Conventional periodontic procedures are excluded from the invention since they are covered by our prior patents.

In carrying out the invention, an aqueous solution of povidone iodine having an available elemental iodine content of about 1-2% by weight of the solution and a peroxide solution, preferably $H_2O_2$, are separately prepared and maintained out of contact with one another since they are incompatible and premature interaction is to be avoided. The aqueous solutions are combined at the time or shortly before they are to be admixed and applied for purposes of chemical sterilization, whereupon the oxygen of the peroxide solution enhances or potentiates the antimicrobial activity of the iodine derived from the povidone iodine. This can be carried out in various ways as will be appreciated from our aforementioned patents, as we have found that chemical sterilization occurs practically on contact of the admixed solutions with the structures or areas to be sterilized or kept sterile. Thus, the dental or surgical operation can be carried out with the antimicrobially enhanced aqueous solution which need only be present for a very short period of time up to a maximum of about 5 minutes or less per application, it being understood that depending on the specific nature of the particular operating procedure it may and frequently is the most effective to apply the freshly admixed solution just prior to carrying out the operating procedure and again applying the chemical sterilizing solution during the operating procedure or after the operating procedure has been completed.

A representative example of the practice of the invention is the high speed drilling of a decayed area of a human tooth within the oral cavity of the patient using standard equipment for the drilling operation and accompanying the same with a trickle or flow of water on the area being drilled. The povidone iodine-$H_2O_2$ solution accompanies or forms a part of the liquid flow onto the tooth so that as drilling proceeds a sterile condition is obtained and maintained since the decayed material which is being removed contains bacteria and viruses which have accumulated to form the decayed or decaying area in the tooth and which, when removed, leaves a cavity which is kept sterile by the flow of chemical sterilizing solution thereinto. Then the cavity is usually dried by air flow, a cotton swab or the like or otherwise treated in the usual manner and the cavity is then filled with a temporary or permanent filling and eventually with gold silver, etc., during all of which period of time sterilization is being effected and maintained. This procedure also tends to reduce the period when future decay may occur and prevents any minute amount of decayed material which might remain as a residue after the drilling operation from starting decay anew.

In a further example of the invention, root canals are cleaned out of decayed, shrunken or deteriorated matter, including deadened nerve structures, in known or conventional manner but accompanied by the application of the chemical sterilizing solution thereto not only to the material being removed therefrom but also to the resulting excavation and the presence of the solution also effects sterilization of the equipment used to clean out the root canal which, before, during and after being cleaned of the material to be removed, and the root canal cavity is flushed with the chemical sterilizing solution and preferably then dried and a filling tamped into place under sterile conditions thereby also retarding any future root canal work which might otherwise be required.

Another embodiment of the invention involves the removal of scale from the surface of teeth, which scale is hard and usually rather firmly attached to the surface of a tooth. In removing such scale in accordance with the present invention, the usual or conventional equipment and technique is followed except that the operating element tip which removes the scale by vibration at very high speed with low amplitude (ultrasonic sound) has a small liquid carrying tube which parallels the descaling element and which by a rubber bulb or other suitable means draws the chemical sterilizing solution from a source thereof and forces its movement by pressure from a suitable source and applies it both to the vibrating descaling element tip and the scale being removed so that sterile conditions are maintained and the future accumulation of scale is retarded.

In accordance with a still further modification of the invention, the artificial structure in or to be positioned in the mouth of the dental or surgical patient is a prosthetic or orthodontic device of per se known construction and placement and the sterilizing solution is applied thereto by spraying or swabbing it on the areas where the devices are to be inserted or affixed and on the devices or areas themselves. The structures may for instance be partial or complete dentures, braces to ensure proper alignment of teeth and to prevent malocclusions. We have found that by applying the chemical sterilizing solution before, during and after the operating procedure, no bacteria, viruses or other undesired microbial matter is trapped or enclosed so that the effective length of life of the prosthetic or orthodontic structure is prolonged while at the same time retarding or preventing the accumulation of undesirable microbial matter.

In addition to the specific operating procedures set forth above, it has further been found that the povidone iodine-peroxide sterilizing solution is highly effective for cleaning and sterilizing dental cavities and dry sockets resulting from dental extractions as well as usefulness for sterilization of intermaxillary fixation devices and the sterilization and cleanliness of implants such as an implanted tooth. In addition, the povidone iodine-peroxide solution has a cleansing and general disinfectant action which results in discouragement of reinfection or reaccumulation of plaque and prolongs the brightness and cleanliness of the surgically inserted prosthetic and orthodontic structure and other devices and surfaces.

What is claimed is:

1. A method of chemically sterilizing artificial structures inserted, constructed, implanted or existing in the human oral cavity and areas thereof exclusive of periodontal procedures, which comprises contacting said structures and areas for a period of time up to about one to two minutes per application on or into all or preselected portions or surfaces of said structures and areas with an aqueous antimicrobially enhanced solution of an iodophor and a peroxide which provides oxygen to enhance the antimicrobial activity of the iodine derived from the iodophor in the solution with at least some of the antimicrobially enhanced solution remaining in contact with such oral cavity structures and areas.

2. A method according to claim 1 in which the articial structures are prosthetic or orthodontic.

3. A method according to claim 1 wherein the areas are decayed surfaces of teeth which have had the decay removed by drilling and thereafter filling the resulting cavity, the drilling and cavity filling being carried out while the enhanced antimicrobial solution is in flushing contact therewith to ensure sterilization and to retard future decay.

4. A method according to claim 1 wherein the areas are formed by dental root canal removal of decayed or infected matter while sterilizing with enhanced antimicrobial solution and filling the cleaned and sterilized canals.

5. A method according to claim 1 wherein the areas are natural teeth having scale which is removed by a suitable dental instrument vibrating at ultra high speed and small amplitude while applying said antimicrobially enhanced solution to the area of the teeth which has has the scale removed so as to effect debriding and sterilizing, 6. A method according to claim 1 in which the iodophor is povidone and the peroxide is $H_2O_2$.

7. A method according to claim 6 in which separate aqueous solutions of povidone iodine and $H_2O_2$ are prepared and maintained out of contact with one another and then mixed and applied to the surfaces of the structures and areas thereof.

* * * * *

UNITED STATES PATENT AND TRADEMARK OFFICE
CERTIFICATE OF CORRECTION

PATENT NO. : 4,738,840

DATED : April 19, 1988

INVENTOR(S) : Gilbert I. Simon and Roy T. Witkin

It is certified that error appears in the above-identified patent and that said Letters Patent is hereby corrected as shown below:

Column 4, line 49; claim 6, second line: -- iodine -- should be inserted after "povidone".

Signed and Sealed this

Thirtieth Day of August, 1988

Attest:

DONALD J. QUIGG

Attesting Officer

Commissioner of Patents and Trademarks